United States Patent [19]

Ellis

[11] 4,454,775

[45] Jun. 19, 1984

[54] CHEMICAL TESTER FOR POOLS

[76] Inventor: Eugene Ellis, 22661 Karam, Warren, Mich. 48091

[21] Appl. No.: 387,103

[22] Filed: Jun. 10, 1982

Related U.S. Application Data

[63] Continuation-in-part of Ser. No. 201,096, Oct. 27, 1980, abandoned.

[51] Int. Cl.³ .............................................. G01N 1/12
[52] U.S. Cl. .................... 73/864.51; 422/68; 422/55
[58] Field of Search ............................ 422/68, 55, 61; 73/864.31, 864.32, 864.51, 864.52, 864.61; 210/514, 515; 119/206

[56] References Cited

U.S. PATENT DOCUMENTS

| | | | |
|---|---|---|---|
| 1,108,561 | 8/1914 | Erickson | 73/864.62 |
| 1,518,160 | 12/1924 | O'Hara | 73/864.61 X |
| 1,728,939 | 9/1929 | Konipol | 73/864.31 X |
| 1,874,395 | 8/1932 | Watts | 73/864.32 X |
| 2,958,222 | 11/1960 | Morgan | 73/864.32 X |
| 2,983,147 | 5/1961 | Morgan | 73/864.32 X |
| 3,841,161 | 10/1974 | Huntington | 73/864.31 |
| 4,083,253 | 4/1978 | Niehow | 73/864.51 |
| 4,196,531 | 4/1980 | Balligand et al. | 73/864.51 X |

FOREIGN PATENT DOCUMENTS 1556082 11/1979 United Kingdom ................. 422/68

Primary Examiner—Kenneth M. Schor
Attorney, Agent, or Firm—Remy J. VanOphem

[57] ABSTRACT

A pool testing device, utilizing a liquid container, includes an elongated handled and a mechanism for detachably and rotatably mounting a liquid container to the handle. A releasing mechanism is also provided so as to actuate the detachably and rotatably mounting mechanism so that the liquid container rotates from a first predetermined position to a second predetermined position when the releasing mechanism is actuated.

11 Claims, 6 Drawing Figures

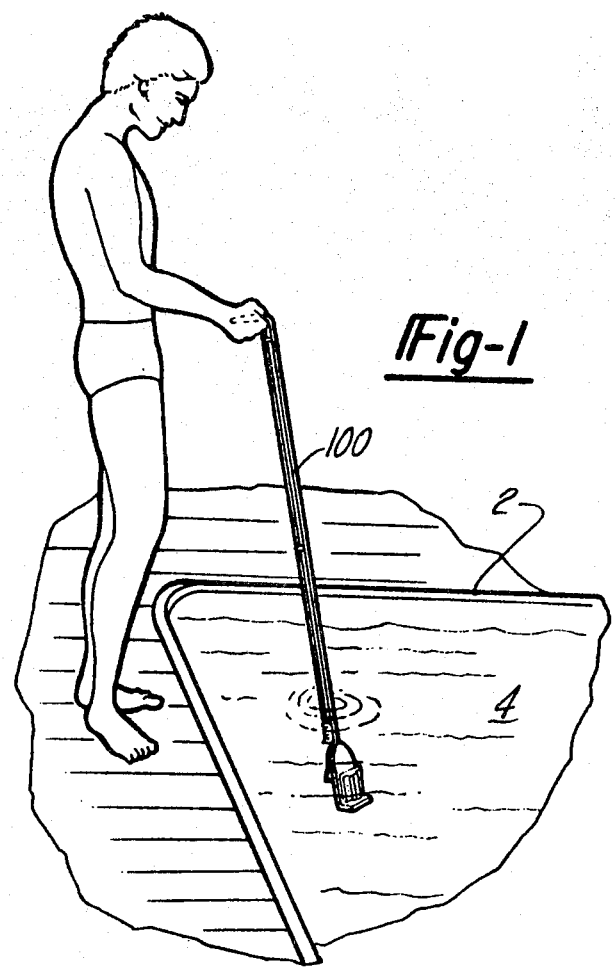
Fig-1
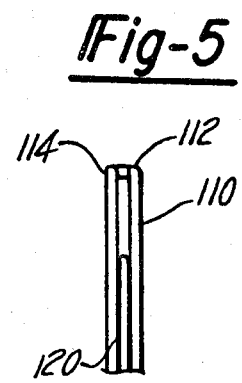
Fig-5
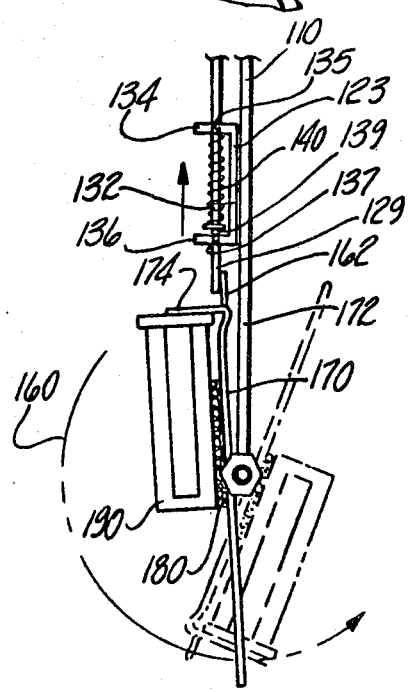
Fig-6
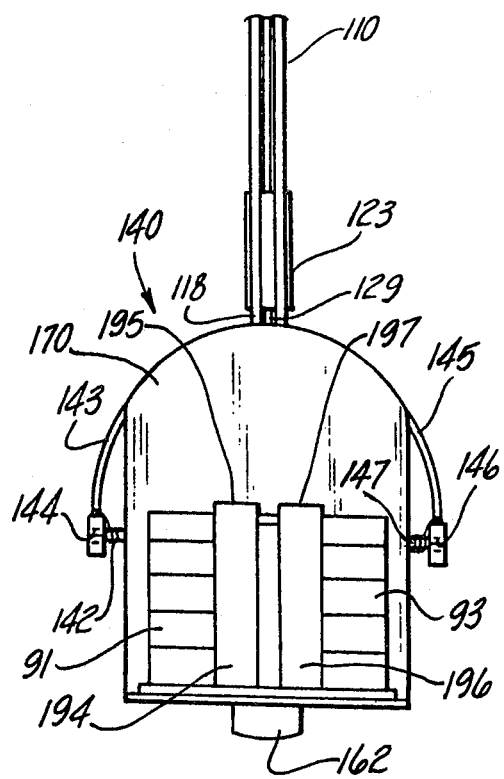

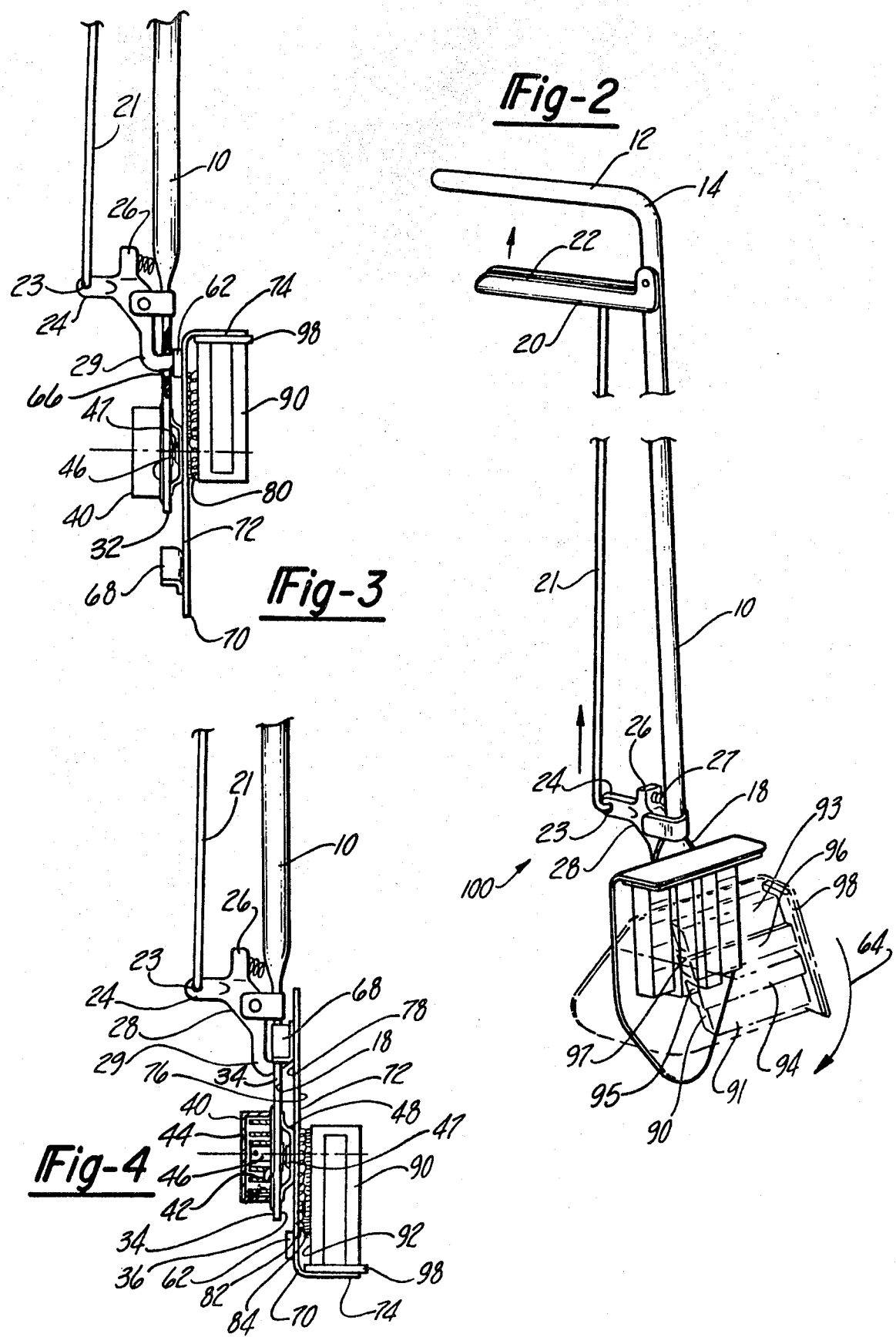

CHEMICAL TESTER FOR POOLS

This application is a continuation-in-part of application Ser. No. 201,096, filed Oct. 27, 1980, and now abandoned.

FIELD OF THE INVENTION

This invention is directed to a tester for pool water which draws a predetermined amount of water at a given depth in the pool into a container having a plurality of compartments so that proper test reagents may be added to each component to check for the acidity, alkalinity and chlorine content of pool water.

BACKGROUND OF THE INVENTION

Over recent years, there has been a surge in the installation of backyard pools. These pools take the form of either inground or an aboveground type of construction. In either type of construction, the pool owner must periodically test the pool water to insure that the water has the proper chemical balance. This periodic check involves testing the water for its acidity or alkalinity which hereinafter is called its pH characteristic. This test is important since an incorrect pH can be responsible for staining or scaling of the pool's walls or the corrosion of metal accessories, such as pumps, ladders, grab rails, etc.

In addition to the pH characteristic, the pool owner must also make sure that there is enough chlorine in the water to maintain water purity. The clorine level of the pool water is affected by a number of factors such as water temperature, evaporation, rain, the number of bathers, etc.

The stability of chlorine in the pool water and its microbicidal activity are pH dependent. Lower pH values cause a more rapid loss of chlorine, thereby increasing the operating cost of the pool. Higher pH values, on the other hand, retard the microbicidal activity of the chlorine even though tests may show its presence in the water.

Since a proper balance of chlorine in the water is essential to kill bacteria and since pH strongly influences this balance, the pH characteristic must not be allowed to change excessively. Therefore, the pool owner must regularly and accurately check the pool water for its acidity, alkalinity and chlorine content.

There are several known prior art fluid sampling devices. For example, U.S. Pat. No. 1,108,561 to Erickson, issued Aug. 25, 1914, discloses a fluid sampling device consisting of an open cup or receptacle adapted to be inserted into a fluid with a scale disposed in proper relation to the cup. In addition, the device has a piston operating in the cup with a plunger operated by the operator's finger with an indicator acting in conjunction with the scale. The device thus permits taking samples in proportion to the quantity of liquid delivered. The device does not provide for simultaneously taking water samples for pH testing and chlorine testing by color comparison.

Carpinello, in U.S. Pat. No. 2,004,568 issued June 11, 1938, discloses another liquid sampling device which is adapted to take samples of liquids at different depths simultaneously. This device does not provide for simultaneously taking samples for pH testing and chlorine testing by color comparison.

Losee in U.S. Pat. No. 2,236,063 issued Mar. 25, 1941, discloses a dipper for taking samples of liquid to facilitate transfer of the sample liquid from the liquid to be tested. The liquid is then transferred to a test tube in which the sample is tested. This device does not provide for simultaneously taking two samples.

Thomson, U.S. Pat. No. 2,624,201 issued Jan. 6, 1953, discloses an elongated rod and holder for an individual liquid sample container such as a test tube. The device releasably holds the test tube at an adjacent one end so that the test tube can be dipped into the liquid in a bulk container to take a sample therefrom. The filled test tube can then be readily removed from the handle and holder device and replaced by an empty test tube for taking a sample from another container.

U.S. Pat. No. 3,692,490 to Hall, issued Sept. 19, 1972, discloses a pool tester which simultaneously withdraws into two separate containers predetermined samples from a given depth in the pool. As the samples of pool water are drawn into the containers, it injects into each sample a given amount of different testing reagent and ejects the water samples tested from each container after the test results are observed. The tester has an extendible handle which, at one end, includes an elongated rectangular housing having a rounded or arcuate side having cylindrical openings. A pair of cylinders are slidably arranged to extend through the top plate into the cylindrical openings. The cylinders are closed at their upper ends by corks or plugs. The lower end of each cylindrical opening is opened to the outside of the housing by ports. Metering blocks are integrally arranged and the lower ends of the cylinders are divided with metering openings. When the sample is to be withdrawn, the cylinders are moved outwardly of the openings in the housing so as to unseat a ball valve thus permitting water to enter into the openings and to inject the reagents into the openings. Thus, the tester dispenses agents from its cylinders in order to sample the fluid to be tested.

The sampling devices to Losee and Thomson are unsatisfactory for pool testing, in that, these testers are unable to withdraw a predetermined amount from a given depth in the pool. On the other hand, the sampling device of Erickson does not permit the simultaneous withdrawing into two separate containers of predetermined quantities of water from a given depth in the pool. Therefore, the Erickson device is not suitable for testing samples of pool water. The liquid sampling devices of Carpinello and Hall, on the other hand, are complex and expensive to make.

SUMMARY OF THE INVENTION

The present invention is directed to providing a liquid sampling device which permits withdrawing into a plurality of containers predetermined samples from a given depth in the pool. In addition, the pool sample container may be removably attached to the sampling device to permit the water samples in each compartment of the container to be tested for acidity, alkalinity and chlorine at a place remote from the pool. Furthermore, the apparatus permits the user to test the pool water at various depths without having to bend or lean over the water so that persons with impaired backs may utilize the apparatus to test the pool water with ease.

The present invention is directed to an apparatus for testing pool water utilizing a liquid container. The apparatus includes an elongated handle having one end and an opposite end. A mechanism is provided for detachably and rotatably mounting the liquid container to the opposite end of the housing. In addition, a releasing mechanism, which is mounted at the one end and extends toward the opposite end of the handle, is provided for releasing the detachably and rotatably mounted mechanism on the opposite end so that the liquid container rotates from a first predetermined position to a second predetermined position when the releasing mechanism is actuated.

It is, therefore, a primary object of the present invention to provide an apparatus for testing pool water having an elongated handle which detachably and rotatably mounts a liquid container to the handle and a mechanism for releasing the detachable and rotating mounting mechanism so that the liquid container rotates from a first predetermined position to a second predetermined position when the releasing mechanism is actuated so that pool water, at a given depth, may be tested easily and accurately.

It is a further object of the present invention to provide a pool water testing apparatus which permits the user to detachably mount a liquid container thereto so that after the user has obtained a sample of pool water at a predetermined depth level, the liquid container may be detached from the apparatus so that the pool water can be chemically tested in the container at a point distant from the pool for its pH value and chlorine content.

It is a still further object of the present invention to provide a pool water apparatus which detachably and rotatably mounts a liquid container to an elongated handle which is simple to use and inexpensive to make.

Other objects and advantages of the invention will become apparent upon reading the following detailed description and upon reference to the drawings.

BRIEF DESCRIPTION OF THE DRAWINGS

FIG. 1 is a perspective view of an observer using the pool tester, according to one of the embodiments of the invention, to sample the pool water;

FIG. 2 is a perspective view of the preferred embodiment of the pool tester according to the present invention;

FIG. 3 is a side view of FIG. 2 with the liquid container in the first predetermined position;

FIG. 4 is a side view of FIG. 2 with the liquid container in the second predetermined position;

FIG. 5 is a frontal view of the pool tester according to the alternate embodiment of the present invention with the handle rotated 90° from its normal position; and FIG. 6 is a side view of the pool tester of FIG. 5.

DETAILED DESCRIPTION OF THE PREFERRED EMBODIMENT

FIG. 1 shows a person using the pool tester according to the present invention which is generally designated by the numeral 100 in a pool 2 having a quantity of water 4 therein. The pool tester 100 may be inserted into the body of the water 4 to any depth desired so that a sample of pool water, at that given depth, may be easily obtained.

FIGS. 2, 3 and 4 show the preferred embodiment of the pool tester 100. The pool tester 100 includes an elongated handle member 10 having a handle 12 at one end 14. A release member 20 is mounted adjacent to the handle 12. The relase member 20 has a finger 22 which is pivotally mounted to the elongated handle member 10. The elongated handle member 10 extends longitudinally from the one end 14 to an opposite end 18. Adjacent to the opposite end of the elongated handle member 10 is mounted a latch member 28 which is pivotally mounted adjacent to the opposite end 18. The latch member 28 has a one end portion 26 and an opposite end portion 29 for a purpose to be described later on herein. The latch member 28 also has a projection member 24 interposed the one end portion 26 and the opposite end portion 29 and extending away from the pivot mount point of the latch member 28. The projection member 24 has an aperture 23 and is fastened therethrough by suitable means for a rod 21. The other end of the rod 21 is fastened to the finger 22 adjacent but spaced away from the elongated handle member 10 for a purpose to be described later herein. The latch member 28 has a biasing member 27 which is interposed between the elongated handle member 10 and the one end portion 26 of the latch member 28.

Also mounted below the opposite end 18 of the elongated handle member 10 and below the latch member 28, is a flat planar member 32 to which is mounted on its one surface 34 a coil biasing member 40. The coil biasing member includes a coil spring 42 which is attached at one end to a cap member 44 and at the other end is attached a pivot pin 46. The pivot pin 46 extends from the cap member 44 so as to project above the opposite surface 36 of the flat planar member 32 below the opposite end 18 of the handle member 10. The cap member 44 is suitably fastened to the one surface 34 of the flat planar member 32 below the opposite end 18 of the elongated handle member 10 by suitable fastening means such as welding or soldering. A spacer member 48 is mounted to the surface 36 of the flat planar member 32 for a purpose to be described later on herein. The spacer member 48 has an aperture therethrough to permit the pivot pin 46 to project through the spacer member 48. A sample holder member 70 is mounted to the pivot pin 46 and the pivot pin 46 has stop means 47 which prevents the pivot pin 46 from moving longitudinally relative to the spacer member 48. The sample holder member 70 includes a flat planar portion 72 and a perpendicular projection member 74 formed perpendicular to the flat planar portion 72. The sample holder member 70 is then mounted to the flat planar member 32 rotatably below the opposite end 18 of the elongated handle member 10 by means of the pivot pin 46. The flat planar portion 72 has a surface 76 to which a separable fastener assembly is attached. One separable fastener member 82 of the separable fastener assembly 80 is fastened to the surface 76 adjacent to the perpendicular projection member 74 by suitable fastening means such as glue or adhesive which is not water soluble. The other separable fastener member 84 is mounted to a sample container 90. The other separable fastener element 84 of the separable fastener assembly 80 is suitably fastened to the opposite end 92 of the sample container 90. The separable fastener members 82 and 84 are well known in the prior art, one such separable element is know by the trademark "Velcro".

The sample container 90 has two sample tubes 94 and 96. The one sample tube 94 is used for obtaining pH readings of the pool water sample and the other sample tube 96 is used for obtaining the chlorine content of the pool water sample. The sample container 90 is detachably mounted to the sample holder member 70 by means of the separable fastener assembly 80 so that a base 98 of the sample container 90 is mounted adjacent or contiguous to the perpendicular projection member 74.

The flat planar portion 72 also has an opposite surface 78. The opposite surface 78 has a first stop member 62 mounted thereto and an oppositely spaced apart second stop member 68. An aperture 66 is formed in the elongated handle member 10 through the flat planar member 32 so as to permit the opposite end portion 29 of the latch member 28 to project therethrough. The opposite end portion 29 engages the first stop member 62 so that when the sample holder member is rotated about the pivot pin 46, the first stop member 62 engages the opposite end portion 29. The opposite end portion 29 is pivotally biased to project through the aperture 66 by the biasing member 27 acting on the elongated handle member 10 and the one end portion 26. The opposite end portion 29 thus engages the first stop member 62 of the sample holder member when the sample holder member is rotated about pivot pin 46 against the urging of the coil spring 42. When the release member 20 is actuated by the user by moving the finger 22 towards the handle 12, the opposite end portion 29 is made to move away from the first stop member 62 thereby permitting the sample holder member 70 to rotate about the pivot pin 46 by urging of the coil spring 42 until the second stop member 68 engages the opposite end 18 to prevent further rotation thereof of the sample holder member 70.

The sample container 90 has sample tubes 94 and 96 which are arranged to project perpendicularly from the base 98 so that the one tube 94 has an opening 95 opposite the base and the other tube 96 has an opening 97 opposite the base 98. The tubes 94 and 96, respectively, are each designed to contain a predetermined amount of fluid so that a measured amount of pool water will be trapped therein. Printed color indicia 91 is adjacent to the one tube 94 and printed color indicia 93 is adjacent to the other tube 96 with varying color indicia standards provided thereon on each side of the tubes 94 and 96 to permit a visual comparison of the pool test water when treated by appropriate chemicals. Those skilled in the art will recognize that the chemical Phenol Red is added to the water sample to test for the pH of the swimming pool water. The addition of a predetermined amount of Phenol Red to a predetermined quantity water sample turns the sample red, with the color depending on the acidity or alkalinity of the water. The observer, after adding the Phenol Red to the water sample in the tube 96 thus matches the color of the sample to the color standard provided on the printed color indicia 93 in order to determine the pH value of the water. On the other hand, Orthotolidine when added to pool water containing chlorine in the tube 94 turns the water to various colors of yellow, depending on the content of chlorine in the water. The darker the color, the higher the chlorine content. Thus, an observer adding a predetermined amount of Orthotolidine to a predetermined sample of pool water containing chlorine thus matches the color on the printed color indicia 91 to determine the chlorine content of the pool water.

When the user desires to use the pool tester 100, the sample container 90 is attached to the surface 76 of the sample holder member 70 by means of the separable fastener assembly 80. The sample container is aligned on the sample holder member 70 such that the base 98 is contiguous or adjacent to the perpendicular projection member 74. The sample holder member 70 is then rotated in a counterclockwise position until the opposite end portion 29 of the release member 20 engages the first stop member 62. In doing so, the user is acting against the coil biasing member 40 so that the coil spring 42 seeks to urge the sample holder member 70 in a clockwise rotational direction 64 as shown in FIG. 2. In this position, the openings 95 and 97 of the tubes 94 and 96, respectively, are positioned to open towards the opposite end 18 of the handle member 10 facing the pool water.

When the user desires to withdraw a sample of the pool water, the user grasps the pool tester 100 by the elongated handle member 10 and inserts the opposite end 18 into the pool water to a predetermined depth such as, for example, 18 inches below the level of the pool water. The user then pulls the finger 22 towards the handle 12 so that the rod 21 causes the latch member 28 to pivot relative to the elongated handle member 10 to compress the biasing member 27. During this operation, the opposite end portion 29 moves away from the opposite surface 78 such that the first stop member 62 no longer engages the opposite end portion 29. When this occurs, the sample holder member 70 rotates about the pivot pin 46 by virtue of the biasing forces of the coil spring 42 to rotate the sample holder member 70 in the direction 64 until the second stop member 68 engages the opposite end 18 of the handle member. The second stop member 68 is oriented on the surface 78 so that after the coil spring 42 rotates the sample holder member 70, the openings 95 and 97 of the tubes 94 and 96, respectively, are oriented toward the one end of the elongated handle member 10.

When the user first inserts the opposite end 18 into the pool water, air is trapped in the openings 95 and 97 of the sample container 90 by virtue of the fact that the openings 95 and 97 are oriented towards the bottom of the pool. However, when the user trips the release member 20, the openings 95 and 97 are rotated so that the openings 95 and 97 are oriented toward the one end of the handle and thus, any air trapped in the tubes 94 and 96 escapes when the sample holder member 70 is rotated and samples of pool water at the desired depth are obtained.

After the samples of pool water are obtained, the user then withdraws the pool tester 100 from the pool and removes the sample container 90 from the sample holder 70 by separating the separable fastener members 82 and 84. The user then performs the desired tests on the pool water, either at pool side or at a place remote from the pool, whichever is most convenient for the user.

The user then injects into the samples a predetermined amount of respective test fluid to each respective sample tube 94 and 96 in order to determine the chlorine content and pH content of the water. When the user is finished with the test, the treated water samples are then ejected from the sample container 90. The sample container is rinsed with tap water to prepare the sample container 90 for the next test.

An alternate embodiment of the invention is shown in FIGS. 5 and 6. In this specification, like parts are designated with like numerals throughout. In this alternate embodiment, an elongated handle member 110 includes a handle 112 which is oriented near the one end 114. The elongated handle 110 extends from the one end 114 towards an opposite end 118. Along the elongated handle member 110 is mounted a release member 120 which includes a finger actuator which is located near the one end 114 of the elongated handle member and a latch member (not illustrated) near the opposite end 118. The release member 120 extends longitudinally from the one end to the opposite end and is suitably fastened along the length of the elongated handle member 110 by a plurality of clips (not shown). One of the plurality of clips (not shown) is positioned adjacent the finger actuator so as not to interfere with the operation of the finger actuator and another of the plurality of clips is positioned midway between the one end 14 and the opposite end 118 of the elongated handle member 110. At the opposite end 118, the release member is fastened to the elongated handle member 110 by means of a C-shaped clip 123 which is suitably fastened thereto. The C-shaped clip 123 has a body portion 132 which is suitably fastened to the elongated handle member 110 by soldering or welding thereto. The C-shaped clip 123 also has two spaced apart extending portions 134 and 136 which are perpendicular to the body portion 132. Each of the extending portions 134 and 136 have an aperture 135 and 137 respectively formed therethrough. An opposite end portion 129 of the latch member extends through the apertures 135 and 137 so as to pass through the C-shaped clip 123. A biasing member holder 140 is mounted around the opposite end 129 of the latch member 128 and is inserted on the C-shaped clip 123 so as to be interposed the extending portions 134 and 136. A pin 139 is suitably fastened to the opposite end 129 of the latch member 128 so that when the release member 120 is actuated by moving the finger actuator 122 towards the handle 112 at the one end of the elongated handle member 110, the opposite end 129 is biased toward the opposite end 118 of the elongated handle member 110.

A biasing member holder 140 is attached to the opposite end 118 of the elongated handle member 110. The biasing member holder 140 includes a pair of arcuate shaped rods 143 and 145. The arcuate shaped rods 143 and 145 are fastened at one end to the opposite end 118 and extend opposite each other. The arcuate shaped rods 143 and 145 at the other end are fastened to a rod 147. The rod 147 thus is positioned perpendicular to the axis of the elongated handle member 110. The rod 147 is inserted at each end through the apertures 144 and 146 in each end of the opposite end of the arcuate shaped rods 143 and 145, respectively, to form a half-circle shape. Thus, the rod 147 is permitted to rotate relative to the arcuate shaped rods 143 and 145. A sample holder member 170 is fastened to the rod 147 by suitable fastening means such as by welding or soldering. The sample holder member 170 is biased to rotate about the rod 147 by means of a spring 142. The spring 142 is fastened at one end to the arcuate shaped rod 143 so as to coil around the rod 147 adjacent to the arcuate rod 143 and then extends across the sample holder member and is wound around the rod 147 adjacent the arcuate shaped rod 145. The spring 142 thus urges the sample holder member 170 to rotate about the rod 147 in the direction 160 as shown in FIG. 6. The sample holder member 170 is similar to the sample holder member 70 as shown in the preferred embodiment except that the sample holder member of the alternate embodiment has only one stop member 162 which extends perpendicular from a projection member 174 and longitudinally from the flat planar portion 172. The stop member 162 is used to engage the release member 120 as will be described later herein. The sample container 190 and the separable fastener assembly 180 are similar to those as described in the preferred embodiment.

The operation of this alternate embodiment is similar to the preferred embodiment except that when the user seeks to use this alternate embodiment, he first rotates the stop member 162 to engage the opposite end 129 of the release member 120. Then he attaches the sample container 190 to the sample holder 170 as in the preferred embodiment. Thus, the openings 195 and 197 of the sample container 190 are oriented toward the pool water and the opposite end 129. The user then actuates the finger actuator by pulling it towards the handle 112 against the biasing force of the spring 142 until the opposite end 129 no longer engages the stop member 162 of the sample holder member 170. When this occurs, the sample holder member 170 is biased in the direction 160 to rotate the sample container 190 until the openings 195 and 197 of the tubes 194 and 196, respectively, are facing towards the one end 114 of the elongated handle member 110. The sample container 190 is oriented in this position after the sample holder member 170 is rotated in the direction 160 because the sample holder member 170 is stopped from rotating more than 180°. This is so because the sample holder member 170 abuts against the opposite end 118 of the elongated handle member 110 when rotated by the spring 142. In all other respects the operation of this alternate embodiment is similar to the preferred embodiment.

What I claim is:

1. An apparatus for testing pool water, said apparatus comprising:

an elongated handle member having one end and an opposite end;

a container for containing liquid said container being disposed adjacent to said opposite end of said elongated handle member, said container having an open end;

rotatable mounting means interconnected with said opposite end of said elongated handle member for rotatably mounting said container to said opposite end of said elongated handle member said rotatable mounting means being rotatable with said container between a first predetermined position wherein said open end of said container faces in the direction of said opposite end of said elongated handle member and a second predetermined position wherein said open end faces in the direction of said one end of said elongated handle member;

selectively detachable mounting means interposed between said rotatable mounting means and said container for detachably mounting said container to said rotatable mounting means;

biasing means interposed between said rotatable mounting means and said opposite end of said elongated handle member, said biasing means biasing said rotatable mounting means towards said second predetermined position;

selectively operable latch means for constraining said rotatable mounting means against the force of said biasing means such that said container is disposed in said first predetermined position; and releasing means, mounted at said one end of said elongated handle member and extending to said opposite end thereof, for selectively releasing said selectively operable latch means so that said container is driven by said biasing means to rotate relative to said elongated handle member from said first predetermined position to said second predetermined position when said releasing means is actuated to release said latch means.

2. The apparatus of claim 1 wherein said rotatable mounting means further comprises:
- a flat planar member mounted to and extending longitudinally from said opposite end of said elongated handle member;
- mounting means, said mounting means being disposed on said flat planar member; and
- a sample holder member, said sample holder member being mounted to said mounting means, said sample holder member further being urged by said biasing means to rotate from said first predetermined position to said second predetermined position.

3. The apparatus of claim 1 wherein said rotatable mounting means further comprises a sample holder member rotatably mounted to said opposite end of said elongated handle member, said biasing means being mounted between said sample holder member and said elongated handle member, said biasing means rotating said sample holder member from said first predetermined position to said second predetermined position.

4. The apparatus of claims 2 or 3 wherein said container is a two liquid sample holder.

5. The apparatus of claim 4 wherein said two liquid sample holder further comprises at least two sample tubes mounted adjacent to one another and indicia printed adjacent to each of said at least two sample tubes.

6. The apparatus of claim 2 wherein said rotatable mounting means further comprises:
- a pivot pin passing through said flat planar portion, said pivot pin further mounted for rotation relative to said flat planar portion and extending longitudinally therefrom; and
- biasing means, mounted to said flat planar member and said pivot pin, for rotating said pivot pin from said first predetermined position about said pivot pin to said second predetermined position.

7. The apparatus of claim 3 wherein said rotatable mounting means further comprises a pivot pin rotatably mounted to said opposite end of said elongated handle member, said pivot pin further being oriented substantially perpendicularly to the longitudinal axis of said elongated handle member; and further wherein said biasing means, are interposed between said sample holder member and said opposite end of said elongated handle member, said biasing means rotating said sample holder member about said pivot pin from said first predetermined position to said second predetermined position.

8. The apparatus of claims 1, 2, 3 or 7 wherein said releasing means further comprises:
- a rod slidably mounted adjacent said elongated handle member, said rod having a one end and an opposite end, said one end of said rod being disposed adjacent said one end of said elongated handle member but spaced a predetermined distance away therefrom and said opposite end of said rod being disposed adjacent said opposite end of said elongated handle member but spaced a second predetermined distance therefrom, said selectively operable latch means being interconnected with said opposite end of said rod; and
- second biasing means for urging said selectively operable latch means to engage said rotatable mounting means in said first predetermined position such that said selectively operable latch means is selectively disengaged from said rotatable mounting means by selectively sliding said rod to overcome the force of said second biasing means.

9. The apparatus of claim 8 wherein said selectively operable latch means further comprises a latch member having:
- an intermediate portion pivotally mounted to said opposite end of said elongated member;
- a one end portion pivotally fastened to said opposite end of said rod;
- an opposite end portion selectively engageable with said rotatable mounting means to selectively secure said rotatable mounting means in said first predetermined position; and
- a portion between said one end portion and said opposite end portion interconnected with said biasing member interposed between said latch means and said opposite end portion of said elongated handle member.

10. The apparatus of claim 1 wherein said selectively operable latch means further comprises a latch member having:
- a first end portion interconnected with said releasing means;
- a second end portion selectively engageable with said rotatable mounting means to selectively secure said rotatable mounting means in said first predetermined position;
- a first intermediate portion disposed between said first end portion and said second end portion and pivotally mounted to said elongated handle member; and
- a second intermediate portion disposed between said first end portion and said second end portion, said biasing means being interposed between said second intermediate portion of said latch member and said opposite end portion of said elongated handle member.

11. The apparatus of claim 1 wherein said container includes at least two sample tubes mounted adjacent to one another.

* * * * *

UNITED STATES PATENT AND TRADEMARK OFFICE
CERTIFICATE OF CORRECTION

PATENT NO. : 4,454,775

DATED : June 19, 1984

INVENTOR(S) : Eugene Ellis

It is certified that error appears in the above-identified patent and that said Letters Patent is hereby corrected as shown below:

Column 4, line 11, delete "for" and insert ---- to ----.

Column 4, line 53, after "member 84" insert ---- of the separable fastener assembly 80 ----.

Column 4, line 55, delete "of the separable fastener assembly 80".

Column 7, line 8, delete "end 14" and insert ---- end 114 ----.

Column 7, line 19, after the numeral "137" insert a comma ---- , ----.

Column 7, line 53, after "arcuate" insert ---- shaped ----.

UNITED STATES PATENT AND TRADEMARK OFFICE
CERTIFICATE OF CORRECTION

PATENT NO. : 4,454,775

DATED : June 19, 1984

INVENTOR(S) : Eugene Ellis

It is certified that error appears in the above-identified patent and that said Letters Patent is hereby corrected as shown below:

In The Claims

Column 10, line 30, delete "member" and insert ---- means ----.

Same line, delete "means" and insert ---- member ----.

In The Abstract

Line 2, delete "handled" and insert ---- handle ----.

Line 5, delete "detachably and rotatably" and insert ---- detachable and rotatable ----.

Signed and Sealed this

Twenty-third Day of July 1985

[SEAL]

Attest:

DONALD J. QUIGG

Attesting Officer

Acting Commissioner of Patents and Trademarks